US012508142B2

(12) United States Patent
Lebolt et al.

(10) Patent No.: US 12,508,142 B2
(45) Date of Patent: Dec. 30, 2025

(54) DYNAMIC TENSIONING REVERSIBLE ORTHOSIS, HAMMOCK STRAP, AND RELATED METHOD OF USE

(71) Applicant: Corewell Health Innovations, LLC, Grand Rapids, MI (US)

(72) Inventors: Jim Lebolt, Grand Rapids, MI (US); Eric VanMiddendorp, Rockford, MI (US); Ian Kovacevich, Carlsbad, CA (US); Nick Gomez, San Marcos, CA (US); Katya Jones, Carlsbad, CA (US); Brian Hatzel, Grand Haven, MI (US)

(73) Assignee: Corewell Health Innovations, LLC, Grand Rapids, MI (US)

( * ) Notice: Subject to any disclaimer, the term of this patent is extended or adjusted under 35 U.S.C. 154(b) by 223 days.

(21) Appl. No.: 18/530,923

(22) Filed: Dec. 6, 2023

(65) Prior Publication Data

US 2024/0180732 A1 Jun. 6, 2024

Related U.S. Application Data

(60) Provisional application No. 63/430,394, filed on Dec. 6, 2022.

(51) Int. Cl.
*A61F 5/01* (2006.01)

(52) U.S. Cl.
CPC .................................. *A61F 5/0118* (2013.01)

(58) Field of Classification Search
CPC ........ A61F 5/37; A61F 5/3746; A61F 5/3753; A61F 5/3723; A61F 5/02; A61F 5/026; A61F 5/0118; A61F 5/022; A61F 5/024; A61F 13/146; A63B 21/4005; A63B 23/02
See application file for complete search history.

(56) References Cited

U.S. PATENT DOCUMENTS

| | | | | |
|---|---|---|---|---|
| 4,735,198 | A * | 4/1988 | Sawa | A61F 13/146 128/878 |
| 5,628,725 | A * | 5/1997 | Ostergard | A61F 5/3746 602/61 |
| 6,106,493 | A * | 8/2000 | Rozell | A61F 5/3738 602/5 |
| 6,306,111 | B1 * | 10/2001 | Dean | A61F 5/3753 602/62 |

(Continued)

*Primary Examiner* — Kari K Rodriquez

(74) *Attorney, Agent, or Firm* — Warner Norcross + Judd LLP

(57) ABSTRACT

A reversible orthosis includes dynamic tensioning elements, recreating and/or improving on the load sharing typically provided by soft tissue, such as ligaments, tendons, muscle and a capsule at a joint of a patient or wearer, thereby providing support and preventing further injury from joint instability and/or joint laxity. The reversible orthosis can support a glenohumeral joint of the shoulder brace and can prevent additional injury from various shoulder instabilities, for example, anterior, inferior, posterior and/or multidirectional instabilities. This can be accomplished by dynamically tensioning posterior, anterior and/or hammock straps of the orthosis. The straps can be primarily adjustable only in tension forces stored there within, rather in orientation relative to the shoulder. This can simplify setup and use, and can ensure the orthosis has a low profile. Related methods of use also are provided.

23 Claims, 10 Drawing Sheets

(56) References Cited

U.S. PATENT DOCUMENTS

| | | | | |
|---|---|---|---|---|
| 8,341,772 | B1 * | 1/2013 | Flores .................... | A41D 31/18<br>2/460 |
| 9,320,635 | B2 * | 4/2016 | Ex-Lubeskie ......... | A61F 5/3723 |
| 10,772,782 | B2 | 9/2020 | Lebolt et al. | |
| 10,792,178 | B2 * | 10/2020 | Alvarez ............. | A63B 21/0442 |
| 2002/0010409 | A1 * | 1/2002 | Bramlage ................. | A61F 5/24<br>602/5 |
| 2006/0167395 | A1 * | 7/2006 | Sawa ........................ | A61F 5/34<br>602/5 |
| 2018/0116893 | A1 * | 5/2018 | Lebolt ................... | A61F 5/0104 |

* cited by examiner

DYNAMIC TENSIONING REVERSIBLE ORTHOSIS, HAMMOCK STRAP, AND RELATED METHOD OF USE

BACKGROUND OF THE INVENTION

The present invention relates to a dynamically tensioned orthosis configured to stabilize a human shoulder joint.

Over time, the joints of a human body invariably are subject to conditions that can lead to joint deterioration, immobility and pain. In some cases, a joint may undergo trauma; in other cases, with age and extensive use, a joint may sustain inherent joint laxity. In both of these cases, the joint can experience a disruption in static and dynamic support.

Human joints can be supported statically, dynamically and via negative pressure. To provide static support, a joint can include soft tissues such as muscles, ligaments, tendons and a capsule. A disruption of any of these static supports, either due to trauma or joint laxity may result in a decrease in the load sharing of those elements. As an example, where a joint ligament is compromised, it likely will be unable to effectively resist joint translation, which in turn can decrease joint stability.

A particular human joint that is prone to disruption due to its complex nature is the shoulder, which comprises the glenohumeral joint. Every year 4.5 million people seek help for shoulder pain, with 2 million seeking help for rotator cuff injuries. Nearly 250,000 people have rotator cuff surgery each year. Over 7.5 million people go to their doctor for a shoulder problem annually, including shoulder and upper arm sprains and strains. Shoulder injury to the rotator cuff, labrum, or other muscles or tendons supporting the glenohumeral joint can lead to shoulder laxity (instability). If a patient has a weakened or unstable shoulder capsule that is not properly supported, it can lead to additional breakdown and injury.

With joint laxity, one will typically require rehabilitation, or, depending on the severity of the injury, surgery to fix the problem. Anterior/inferior instability is the most common problem (about 60%), and posterior instability (about 20%) is less common but does occur most frequently in football lineman. Multi-directional instability makes up the remaining 20% or so of cases.

The glenohumeral joint of the shoulder is invariably unstable due to the convex articulation of the humeral head with the concavity of the glenoid fossa. The humeral head is covered by less than a third of the glenoid fossa throughout the joint's entire range of motion. While the glenohumeral ligaments, labrum and capsule as well as the articular surface provide static support. These tissues can be disrupted due to traumatic injury or over time with inherent joint laxity. Accordingly, such compromised ligaments are unable to effectively resist joint translation, which decreases joint stability. Specifically, the inferior glenohumeral (GHL) (with its anterior and posterior bands), the superior GHL, and the coracohumeral GHL are all important components of the complex. When these respective ligaments are compromised, this can lead to anterior, posterior, inferior and/or multidirectional shoulder instabilities.

The most common cause of shoulder pain in athletes, and in particular young athletes, is shoulder instability and not, as frequently misdiagnosed some underlying rotator cuff injury, impingements or bursitis. Rotator cuff injuries for youth athletes are extremely rare, whereas instability is common. (Savatsky, Gary, MD. "Shoulder Instability." Anterior Shoulder Instability (n.d.): n. pag. www.ossmc-.com. 1 May 2006. Web. 9 Sep. 2015.)

To address shoulder instability, due to trauma, failed surgery or inherent joint laxity, or to protect or rehabilitate a successfully, surgically repaired shoulder, many healthcare providers resort to supporting the shoulder joint with an external orthopedic stabilization device. Such a device can provide external static, as well as dynamic, support to enable the individual to return to a previous level of function and hopefully reduce the risk of repeated injury. While there are a number of such devices in the market, many are complicated to use, have easily disrupted, misplaced or removed straps, and require a healthcare provider knowledgeable in the force vectors associated with particular instabilities to consistently install the device, particularly where the straps float over the shoulder. Further, most conventional shoulder braces do not address all forms of instability, for example, each of anterior/inferior instability, posterior instability, and straight compression laterally as well.

One shoulder brace that addresses issues from above is described in U.S. Pat. No. 10,772,782 entitled DYNAMIC TENSIONING ORTHOSIS AND RELATED METHOD OF USE, filed on Oct. 27, 2017 to Lebolt et al, which is hereby incorporated by reference in its entirety. However, there are further orthosis enhancements and variations that can address issues with conventional shoulder braces while providing additional features, such as improved usability and additional support.

SUMMARY OF THE INVENTION

A shoulder orthosis and related method of use to provide support and prevent additional injury from joint instability is provided.

In one embodiment, a reversible orthosis is provided in the form of a shoulder brace. The should brace includes static and dynamic tensioning elements, recreating and/or improving on the load sharing typically provided by soft tissue, such as ligaments, tendons, muscle and a capsule at a joint of a patient or wearer, thereby providing support and/or preventing additional injury from joint instability. The shoulder brace can provide support and prevent additional injury from various shoulder instabilities, for example, anterior, inferior, posterior and/or multidirectional instabilities. This can be accomplished by applying anterior, posterior and lateral dynamic tensioning on the wearer's shoulder via the brace. The reversibility of the shoulder brace allows it to support either the left or the right shoulder depending on how it is worn.

The reversible shoulder orthosis can include a symmetrical base comprised of a vertically symmetrical compression mitt and vertically symmetrical Torso strap, along with individually and separately tensioned resistance straps. The straps can include an anterior wind-up strap and a wind-up posterior strap. The straps can extend through a symmetrical anchor or low-profile tunnel that enables the straps to overlap and slide within the channel, and that allows the direction of tension within the straps to be controlled, but that prevents the straps from sliding across the base to different orientations or along different routes that alter the tension force vectors exerted by the orthosis on the glenohumeral joint.

The anterior strap and posterior strap can originate on the respective anterior or posterior of the reversible base, extend downward inferiorly, and wind under the arm to provide support. The anterior strap can originate on the front of the shoulder or anterior of the base, wind approximately 180 degrees around and under the wearer's arm, and terminate laterally or posterior to the wearer's humerus or upper arm. This anterior strap can provide posterior support and also anterior/inferior support. The posterior strap can originate on the back of the shoulder or posterior of the base, wind approximately 180 degrees around and under the wearer's arm, and terminate laterally or anterior to the wearer's humerus or upper arm. This posterior strap can provide anterior/inferior support and also posterior support.

In one embodiment, the shoulder brace is reversible such that it can be utilized as a left shoulder brace or a right shoulder brace. The reversible shoulder brace is modular and can be formed by joining the shoulder compression mitt and torso strap, which are each generally symmetrical along a vertical axis. The mitt and torso strap can be connected via hook and loop connectors and because of the vertical symmetry, the shoulder brace is reversible and functional to provide suitable support and bracing for the left or right shoulder. The torso strap can have multiple panels that can be individually removably or selectively joined with the compression mitt to form the reversible base.

In one embodiment, the shoulder brace includes an adjustable bicep strap that can be guided by an anchor disposed on the sleeve. The anchor can include a channel for routing the adjustable bicep strap. The bicep strap can wrap around the wearer's arm and be dynamically tensioned at a desired level. The support can supplement the tension forces provided by the other features of the shoulder brace. Further, the adjustable bicep strap can overlap the ends of the posterior and anterior wind-up straps providing additional support to keep the ends of those straps secured in place on the sleeve while the opposite ends of the anterior and/or posterior straps are unsecured to adjust the dynamic tension stored therein.

To equip the shoulder brace, a user can place either arm in the shoulder mitt sleeve of the brace, and pull the brace toward their neck to ensure proper location of the straps. Then, the brace can be closed by wrapping the torso strap around the chest and securing the hook and loop panels. Next, the user can wrap the hook and loop bicep closure around the bicep and secure it to the sleeve of the brace. The anterior wind-up strap can be tensioned by pulling the strap and securing the hook and loop fastener on the front of the base or torso strap near the axilla of the unbraced arm. The posterior wind-up strap can be tensioned by pulling the strap and securing the hook and loop fasteners on the back of the base or torso strap near the axilla of the unbraced arm. Both the anterior and posterior wind-up straps can be adjusted as needed to provide a suitable amount of stability and support. For example, tension in the anterior wind-up strap can be increased for users with posterior instability. Equipping the shoulder brace on the opposite shoulder follows a mirrored procedure beginning with the user placing their opposite arm in the shoulder mitt sleeve of the brace.

In one embodiment an optional hammock strap can be installed on the shoulder brace to provide additional anterior/inferior support. To install the hammock strap, bifurcated ends of the hammock strap are routed through shoulder loops on the mitt and secured with hook and loop fasteners near the center of the user's back. For suitable support, the crease on the hammock strap, which marks the bifurcation, is positioned near the front of the axilla and lateral border of the pectoralis. To complete installation of the hammock strap, the free end is pulled under the axilla of the braced arm and secured with hook and loop fasteners on the back. Alternatively, the free end of the hammock strap can be pulled around to the front, under the unbraced arm, to provide a desired level of support. The strap generally provides anterior/inferior support and can be adjusted as desired to provide a desired level of stability.

The current embodiments provide an orthosis and related methods of use that can comprehensively support a wearer's joint during movement, regardless of the type of instability in the wearer's joint. In some cases, the brace is reversible, and its wind-up straps can be preconfigured on fixed, static routes across the brace so that the tension, rather than the location or orientation, of the straps can be altered or modified to address a particular instability on either shoulder. This can greatly simplify the donning and installation of the orthosis on the wearer. The hammock strap can be optionally included in some embodiments to provide additional support.

The orthosis also can functionally stabilize and assist the wearer based on their specific instabilities or conditions. The orthosis can have multiple use cases, including wearing the orthosis prophylactically to prevent injury, wearing the orthosis post-injury to continue working at an occupation or to extend an athlete's season, and also wearing the orthosis post-surgery for increased support and rehabilitation.

Multiple different configurations of the shoulder brace can be provided by varying the configuration and/or presence of the anterior wind-up strap, posterior wind-up strap, and hammock strap. A rotator cuff configuration can be provided by providing generally equal tension on the anterior wind-up strap and the posterior wind-up strap. In this rotator cuff configuration, the hammock strap can be optionally installed depending on whether or not additional anterior/inferior support is desired. This rotator cuff configuration can also be utilized to provide a posterior instability configuration or multidirectional instability configuration depending upon the tensioning of the straps. This configuration can provide additional support for overhead workers. Another configuration relies on the inclusion of the hammock strap. That is, relatively equal tensioning can be provided on the anterior wind-up strap and posterior wind-up strap while also utilizing the hammock strap to provide additional anterior/inferior support.

The orthosis can be helpful in that it is fully functional, allowing a full range of motion while providing support for any form of shoulder instability, including anterior, inferior, posterior and/or multidirectional instabilities. Thus, the orthosis can be helpful in addressing one or more instabilities or laxity of the shoulder joint. The orthosis also can support a user who has damaged the supporting structures of the shoulder capsule or experienced one or repeated glenohumeral subluxations or dislocations. Optionally, the orthosis restrains the humeral head from anterior, posterior and inferior translation, and/or applies compression to the glenohumeral joint. The orthosis also can stimulate proprioceptive awareness of movement of the glenohumeral joint.

When used in sports, the orthosis can be worn by football, rugby, lacrosse and hockey players. Of course, virtually any other athlete can wear the orthosis as well. For example, basketball or soccer players with repeated subluxation, instability, or dislocations may wear this brace but less frequently. In addition, manual laborers and other workers can utilize the orthosis to assist in movement and comfort of an affected joint.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENTS

Figure 12:
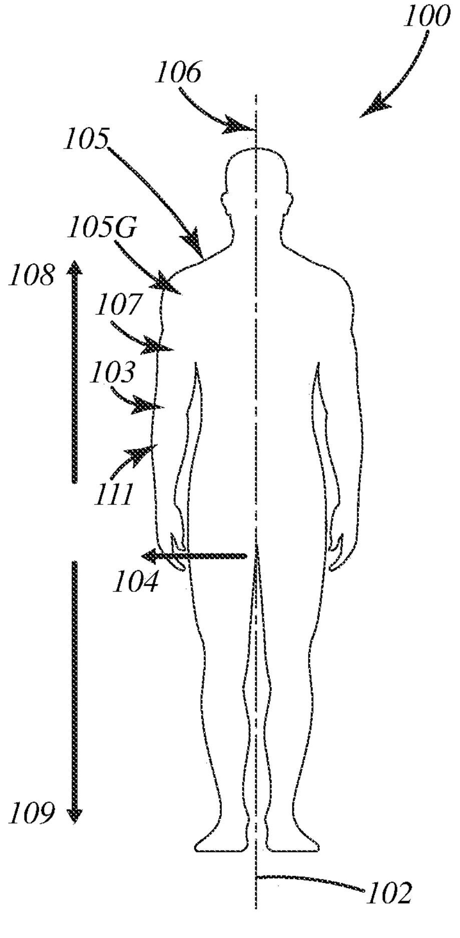
FIG. 12 is a front view of a wearer illustrating directions relative to features in association with the wearer's anatomy.
Figure 13:
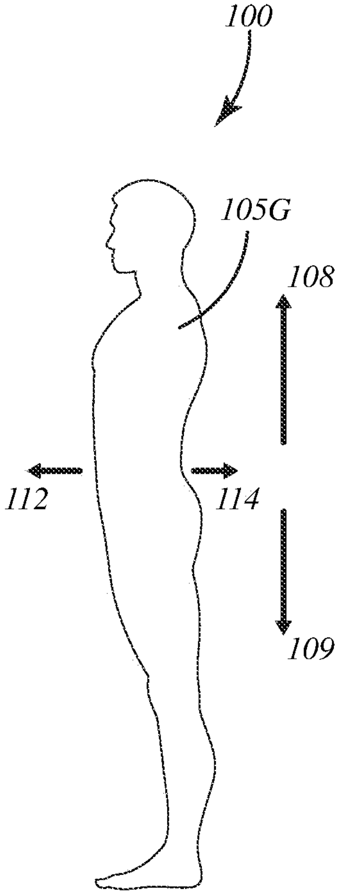
FIG. 13 is a side view of the wearer illustrating directions relative to features in association with the wearer's anatomy.

A current embodiment of the reversible orthosis is illustrated in FIGS. 1-11, and generally designated 10. The orthosis shown in the current embodiment is in the form of a shoulder brace, configured to dynamically stabilize and support the glenohumeral joint 105G in a shoulder 105 of a wearer 100 (FIGS. 12-13).

Generally, the orthosis 10 includes a reversible base 20 including a compression mitt 280, a sleeve 30, and a torso or torso strap 31. The compression mitt 280 and sleeve 30 can be integrally formed. The torso strap 31 and compression mitt 280 can be fastened with hook and loop fasteners to form the reversible base 20.

Figure 4:
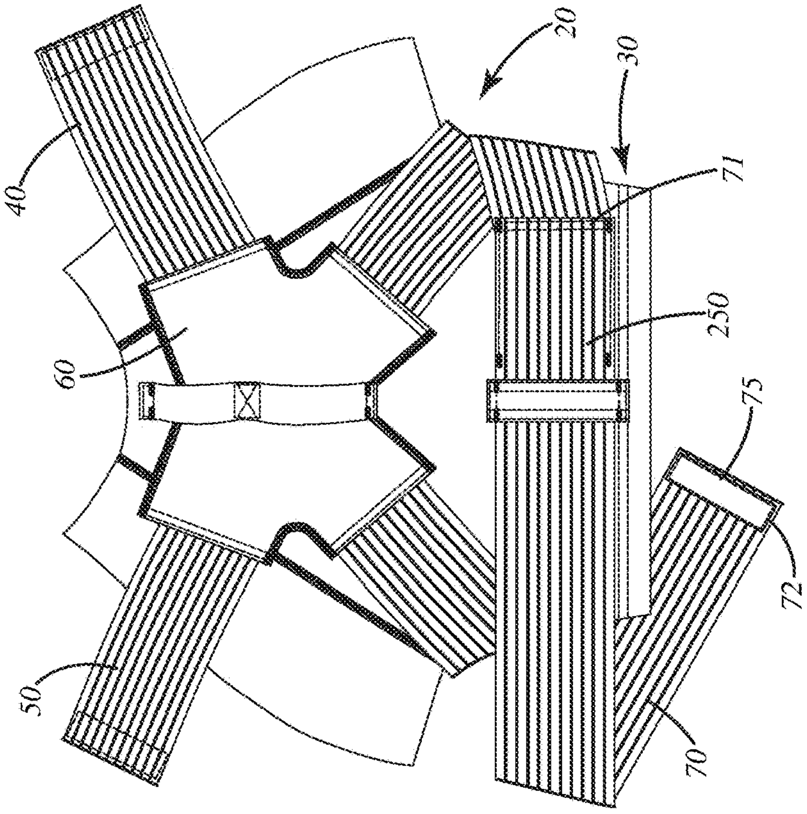
FIG. 4 is a top view of the shoulder brace to illustrate attachment and routing of the bicep closure strap.
Figure 3:
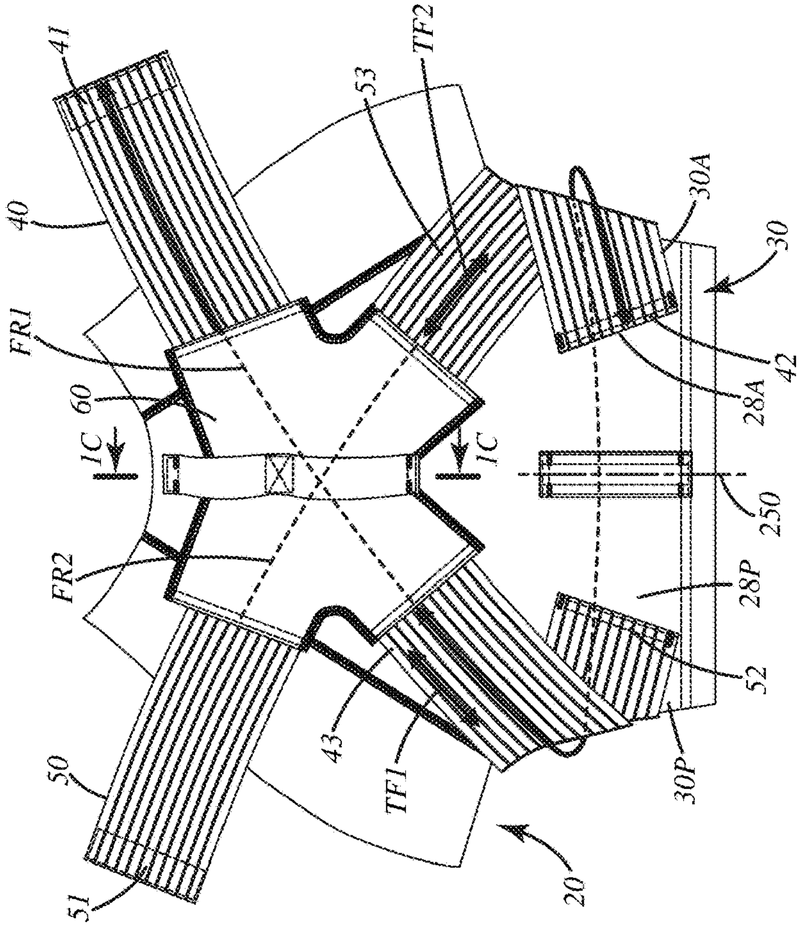
FIG. 3 is a top view of the shoulder brace to illustrate the attachment and routing of the wind-up straps without the bicep closure strap attached.

The reversible base 20 can secure the orthosis to the torso 113, while the sleeve 30 can secure the orthosis to the arm and over the shoulder 105. An anterior strap 40 and a posterior strap 50 are secured to the reversible base 20, and wrap around the arm as further described below. Perhaps as best illustrated in FIGS. 3 and 4, the anterior strap 40 and posterior strap 50 are both guided along respective fixed routes or pathways by a shoulder anchor 60. Referring to FIG. 3, the anterior strap 40 pathway is labeled FR1 and the posterior strap 50 pathway is labeled FR2. Optionally, the anterior strap and posterior strap are fixed and permanently constrained along these fixed routes FR1 and FR2 so that the wearer cannot deviate or modify those routes relative to the underlying base 20. In some applications, the anchor 60 can be movable and/or replaceable along the exterior of the base to facilitate such modification.

The anterior 40 and posterior 50 straps can be constructed from an elastic material and can be primarily adjustable only in tension force stored in those straps, that is, they optionally cannot be significantly reoriented or moved around relative to other portions of the base. With this construction, a wearer or user can adjust the tension forces TF1 or TF2 in the respective anterior 40 and posterior 50 straps to provide a desired dynamic tensioning of those straps and attendant support to the glenohumeral joint 105G. A user need not be concerned with where the ends of the straps are located or anchored to the base because the respective anchors, as discussed below, are relatively fixed in their spatial orientation relative to one another, as are the ends of the straps.

Referring to FIGS. 12-13, any reference to body position or direction herein can be made with respect to the body 100 of a wearer in the anatomical positions there. References to the position of the orthosis 10 with respect to body 100 of the wearer, as well as references to movement can be made using standard anatomical position and movement terms. For example, the term superior 108 is a direction closer to a head of the wearer, the term inferior 109 is a direction farther from the head of the wearer, the term medial describes a direction 106 closer to the midline or sagittal plane 102 of the body 100, while the term lateral describes a direction 104 is farther from the midline or sagittal plane 102. The term anterior 112 describes a direction toward the front of the body 100 and the term posterior 114 describes a direction toward the back of the body 100. When describing bodily movements, abduction describes motion away from midline 102, and the term adduction describes motion toward midline 102. Flexion refers to motion that reduces a joint angle, and extension refers to motion that increases a joint angle.

The shoulder 105 includes the glenohumeral joint 105G which is relatively complex and capable of rotation in multiple planes when the arm is moved relative to the torso 113. As exemplary types of rotation, "external rotation" or "internal rotation" of the shoulder 105 occurs when the forearm or lower arm 111 is respectively displaced away from or toward the torso 113 while the position of the upper arm 107 is maintained fixed against the side of the torso 113 and the elbow 103 is flexed at 90°. "Abduction" or "adduction" of the glenohumeral joint 105G occurs when the upper arm 107 extends outward to the side and displaces away from or toward the torso 113. "Flexion" or "extension" of the joint 105G occurs when the entire arm 107, 103, 111 is extended forward and is displaced respectively toward or away from the torso 113.

The components of the reversible orthosis 10, focusing largely on the base 20 components, include the vertically symmetrical compression mitt 280, vertically symmetrical torso strap 31, stability straps 40 and 50, as well as the symmetrical anchor, which will now be described in further detail.

As shown in FIGS. 1A-B, 7A-B, 10, and 11, one embodiment of the orthosis 10 includes an integral shoulder compression mitt 280 including a shoulder-sleeve compression knit section 30 and an elastic section 63. This mitt, and perhaps more specifically the shoulder-sleeve compression knit section 30, can provide uniform tension and can pull the humeral head directly into the glenohumeral joint. The compression knit section 30 also can provide resistance across the anterior and posterior of the shoulder, as well as across the top of the shoulder to produce an evenly distributed tension or force across the shoulder. The elastic section 63 can include an anterior surface 22 and posterior surface 24 (e.g., a hook reception landing zones) which can be disposed respectively across a portion of the anterior and posterior of the wearer's torso 113. The anterior surface 22 and posterior surface 24 can each be respectively joined (e.g., stitched) with suitable sections of the elastic section 63. These components can be integral with one another or can be stitched portions of textile or performance material. Some suitable materials from which the base and sleeve can be constructed can include Neoprene, BIOSKIN™ available from Bio Skin of Ashland, Oregon, knitted or woven fabrics, engineered mesh, engineered textiles, and similar materials that are generally breathable and durable.

Optionally, the mitt can be configured to provide a "hard stop" to arrest external rotation of the humeral head and generally the shoulder. As an example, when the mitt is properly placed over the wearer shoulder, and the shoulder begins to externally rotate, the mitt can prevent that rotation beyond a certain angular orientation that may be detrimental to the structure and or condition of the glenohumeral joint 105 and/or the humeral head. For example, the mitt can be configured to prevent external rotation beyond a certain angular orientation, such as beyond 20°, beyond 30°, beyond 40°, beyond 50° or other angles, depending on the condition of the user's shoulder and glenohumeral joint. To provide this hard stop to external rotation, the intermediate parts 43, 53 of the anterior and posterior straps 40, 50 can be constructed from elastic material that only stretches a certain amount, then ceases stretching. Thus, when those elements are stretched to a predetermined amount, they will stretch no more. This, in turn, will arrest the external rotation and provide the hard stop via the mitt. Of course, as desired, this hard stop feature of the mitt can be modified or even deleted from the orthosis, depending on the application.

Figure 11:
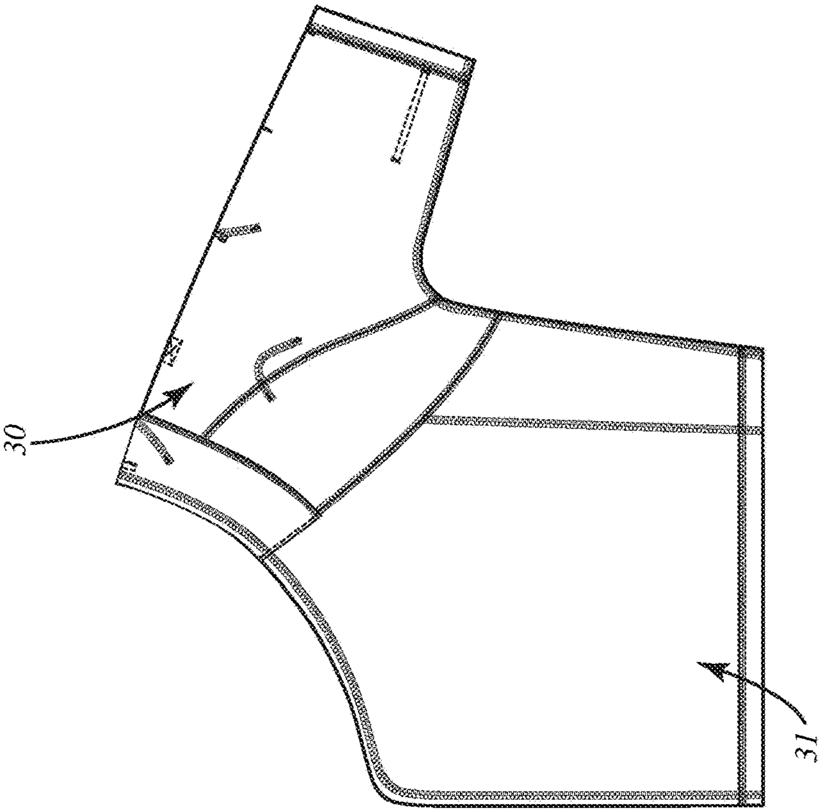
FIG. 11 is an interior view of the portion of the shoulder brace shown in the front exterior view of FIG. 10.
Figure 10:
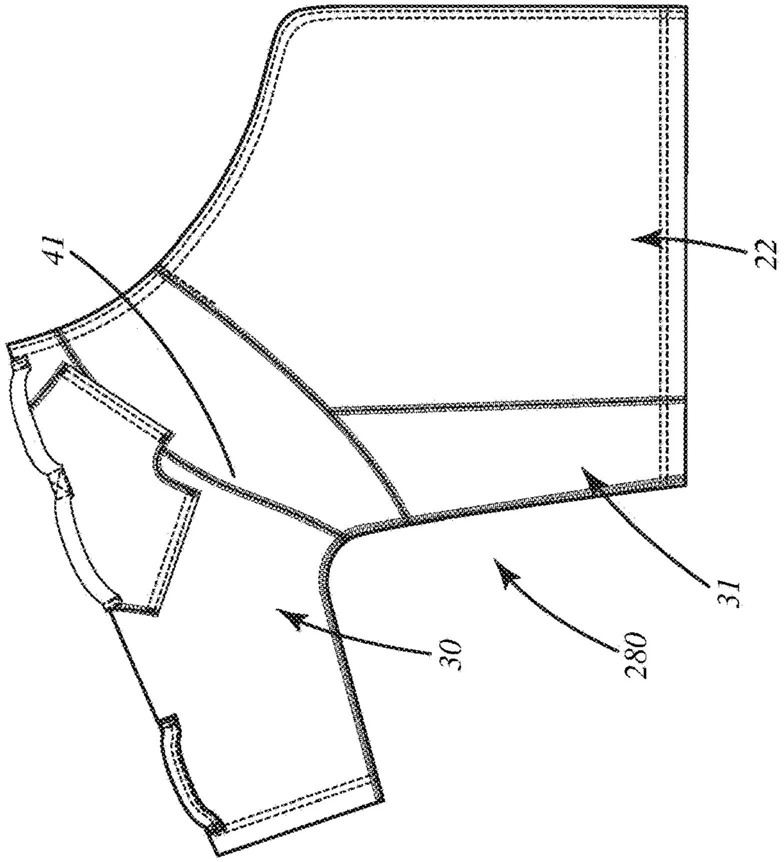
FIG. 10 is a front exterior view of the shoulder brace without straps.

Perhaps as best shown in FIGS. 10-11, the compression mitt 280 can include several components that are permanently stitched together. For example, as depicted in the current embodiment, the compression mitt 280 can include a shoulder-sleeve compression knit section 30 having a Raglan sleeve stitch 41 to assist in formation of the reversible base 20 armhole and an elastic fabric (e.g., elastic polyurethane or LYCRA®) section 63. Two stretch loop fabric sections (e.g., the compression mitt anterior and posterior sections 22, 24) can be sewn to the front of the LYCRA sections, one on the anterior side and one of the posterior side of the base.

Figure 1B:
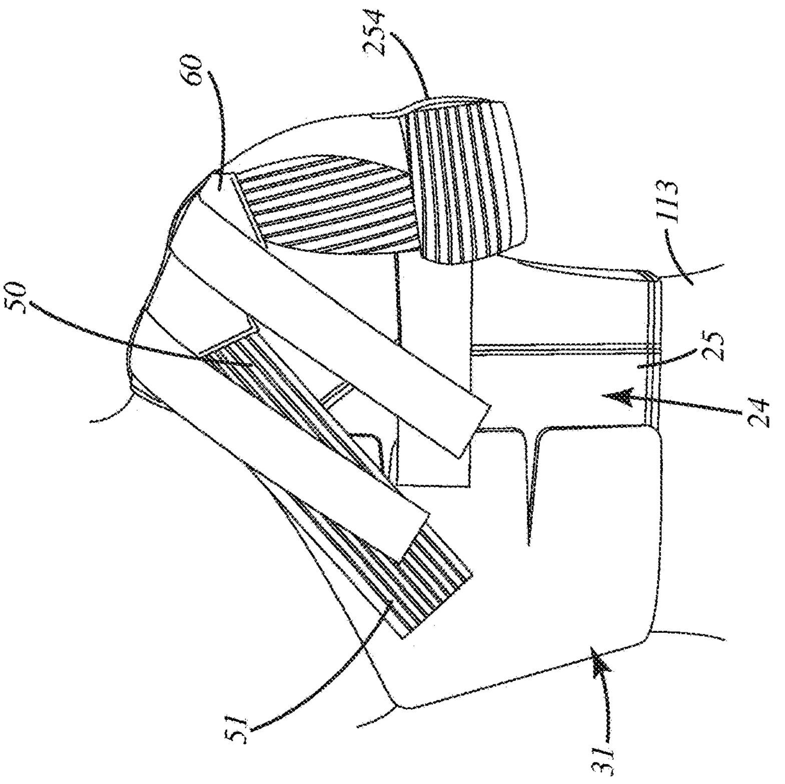
FIG. 1B is a rear perspective view of the reversible orthosis of FIG. 1A.
Figure 1A:
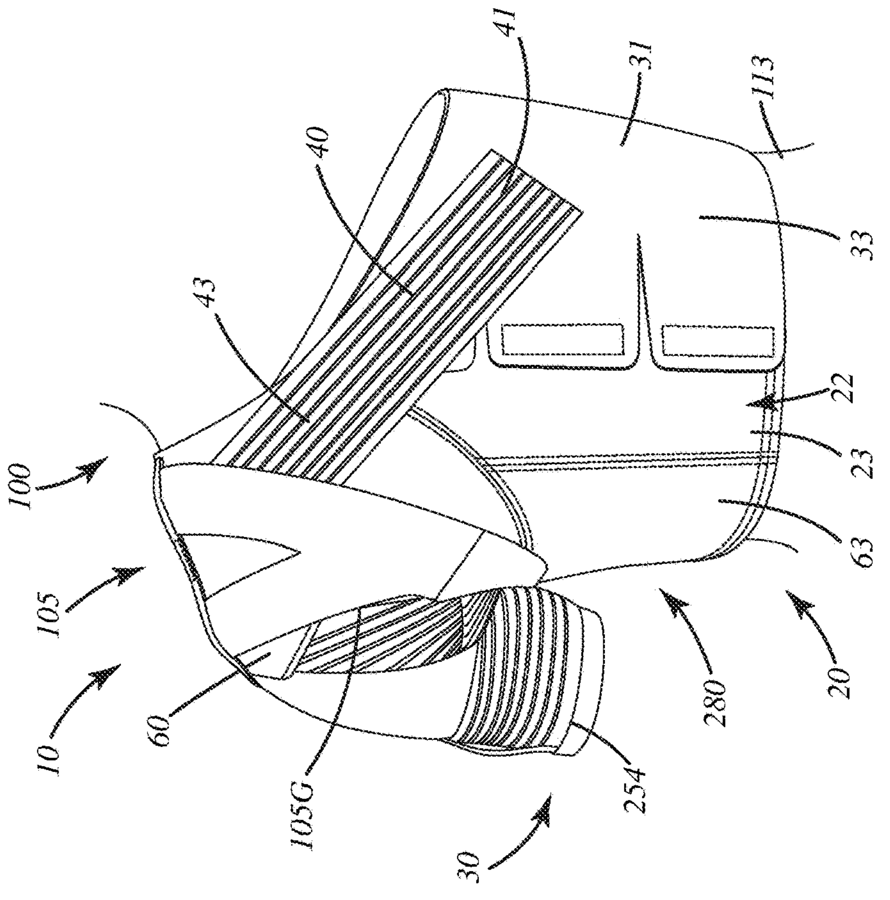
FIG. 1A is a front slight perspective view of the reversible orthosis in the form of a shoulder brace of a current embodiment, while installed on a right shoulder.

Perhaps as best shown in FIGS. 1A-1B, the shoulder-sleeve compression knit section 30 can extend adjacent and/or over the base anterior 22, superiorly upward and over the shoulder 105, and then inferiorly downward adjacent the base posterior 24. This section 30 can be at least partially disposed superior to the anterior deltoids, the lateral deltoids, and the posterior deltoids of the wearer. The shoulder-sleeve section can be stitched, sewn, fastened, or integrally formed with some or all of the other compression mitt components, for example, the elastic fabric section 31.

The sleeve-shoulder portion 30 of the compression mitt 280 can be constructed from a different material than the remainder of the base 20. For example, the shoulder-sleeve portion can be constructed from a flexible material that is more rigid than the flexible section 31. In a further example, the sleeve-shoulder portion can be constructed from neoprene, while the remainder of the base can be constructed from a textile fabric or a thinner, more flexible material. In some embodiments, a bolster element can be provided in the form of a silicone insert or plastic panel that is sewn into or otherwise disposed in or adjacent the base 20, optionally superior to and/or closer to the sagittal plane 106 than the above noted stability straps.

Figure 2B:
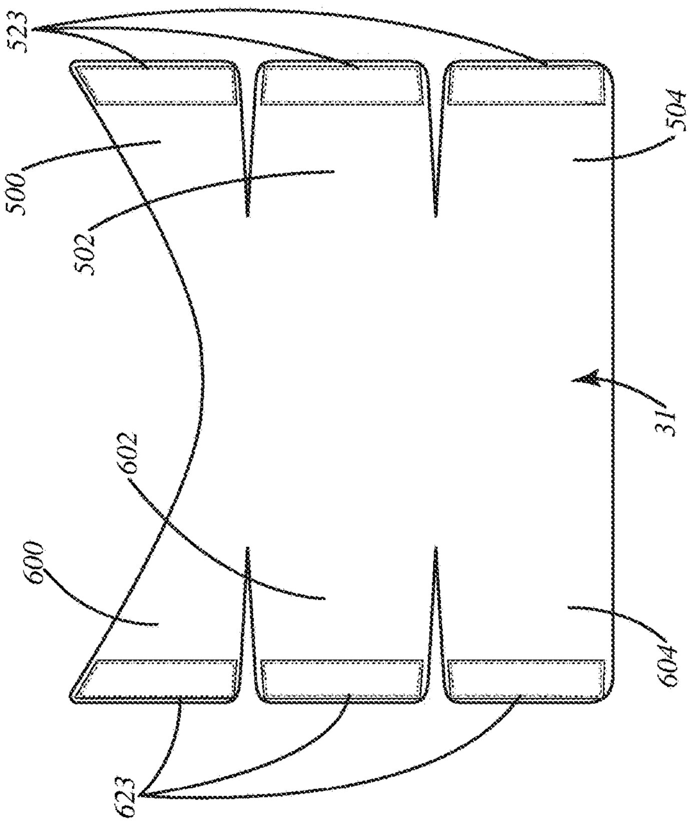
FIG. 2B is a back view of the symmetrical base of FIG. 2A.
Figure 2A:
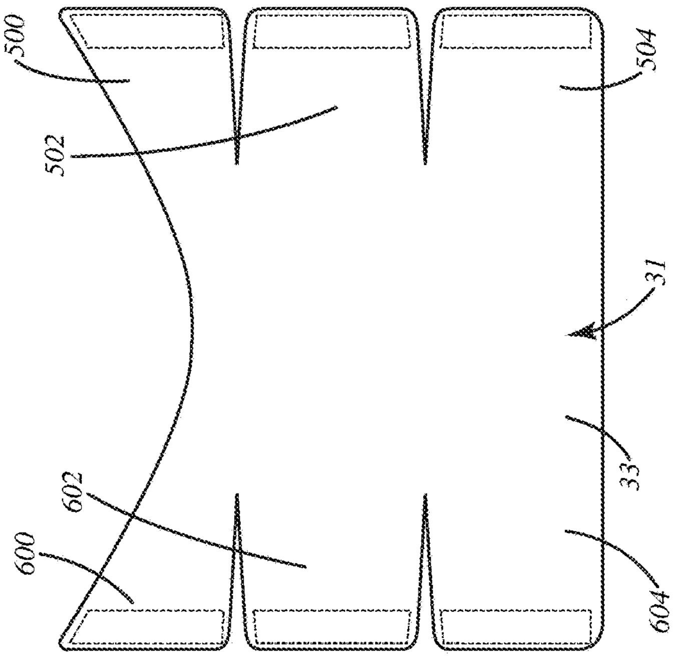
FIG. 2A is a front view of the symmetrical base having hook and loop fastener panels.

As shown, the compression mitt 280 can be selectively joined around the user's torso with the torso strap 31 using hook and loop fasteners. In the depicted embodiment, the compression mitt anterior 22 includes a portion 23 of counterpart hook or loop fasteners and the compression mitt posterior 24 includes another portion 25 of counterpart hook or loop fasteners. Perhaps as best shown in FIG. 2B, the torso strap 31 includes six symmetrical panels: three anterior torso strap panels 500, 502, 504 and three posterior torso strap panels 600, 602, 604. Each of the torso strap panels includes a portion 523, 623 of hook or loop fasteners that can close and secure the respective ends of the torso strap 31 to the compression mitt 280 as depicted in FIGS. 1A-B. For example, the compression mitt can include an anterior loop surface or zone 23 and a posterior loop surface or zone 25 for connection with respective hook or loop surfaces of the torso strap 31. Although the current embodiment utilizes hook and loop fasteners, in other embodiments the fasteners can be buttons, clips, clasps, buckles and the like. Further, the hook and loop portions can be reversed. Optionally, the fasteners can be deleted, and the reversible base can be in the form of a shirt having the compression mitt 280 and torso strap 31 permanently stitched together. Because the torso strap 31 and compression mitt 280 are generally symmetrical along a vertical axis, when joined together to form the base 20, the orthosis is reversible because it can be donned by a user's left or right shoulder. As shown in FIG. 2A, the front exterior surface or portion thereof of the torso strap 31 can be covered with a hook or loop surface 33 to serve as a selective connection point for the anterior and posterior stability straps.

Figure 5:
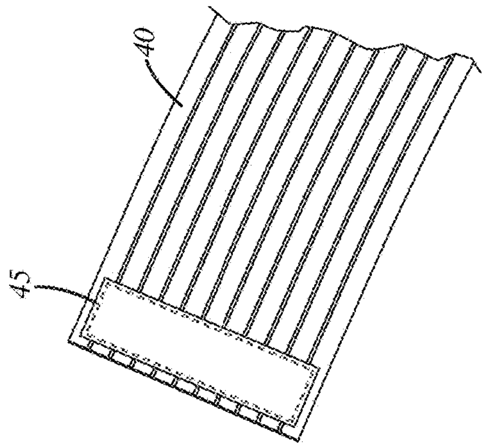
FIG. 5 is a close-up view of one end of a strap of the current embodiment.

In the current embodiment, both ends 41, 42 of the anterior stability strap 40 can include a hook or loop surface for anchoring the end of the strap to the base. For example, as shown in FIG. 5, an end of the anterior stability strap 40 can include a portion of hook tape 45 joined to the end of the strap to facilitate selective joining of the end of the strap with a counterpart loop fastener. Similarly, in the current embodiment, both ends 51, 52 of the posterior stability strap 50 can include a hook or loop surface to facilitate selective connection to the base.

Perhaps as best shown in FIG. 1A, the anterior stability strap 40 can be selectively secured at its first, medial, end 41 to the base 20, in particular to the outer anterior surface 23 of the compression mitt 280 or the outer surface 33 of the torso strap 31. As shown in FIG. 3, the anterior stability strap 40 can also be secured at its second, lateral, end 42 to the base 20, in particular to the outer anterior surface 28A. For example, the anterior stability strap can be joined to the sleeve in the form of stitching, glue, cement, a hot weld, fasteners, or other devices to fixedly and permanently secure the lateral end 42 to the sleeve 30. By permanently secured or permanently joined, it means herein that the end or component cannot be removed from the base or other component without destroying, damaging or impairing one or both of those components. The phrases "permanently secured" or "permanently joined" also can be used in conjunction with the joining of other elements of the orthosis as described below.

Optionally, the tension force in this anterior strap can increase during external rotation and abduction to provide a "wind-up" effect, which also can increase proprioception, during external rotation and abduction, typically a vulnerable position for a wearer with anterior/inferior instability. In turn, the wearer can better perceive the vulnerability in that position due to the tension in the strap.

Perhaps as best shown in FIG. 1B, the posterior stability strap 50 can be secured at its first, medial, end 51 to the base 20, and in particular to the outer posterior surface 25 of the compression mitt 280 or the outer surface 33 of the torso strap 31. As shown in FIG. 3, the posterior stability strap 50 can also be secured at its second, lateral, end 52 to the base 20, in particular to the outer posterior surface 28P. For example, the lateral end of the posterior strap 50 can be permanently joined to the sleeve 30 in the form of stitching, glue, cement, a hot weld, fasteners, rivets or other devices to fixedly and pivotally secure the secondary posterior end 52 to the sleeve.

Perhaps as best shown in FIGS. 3 and 4, the base 20 includes a sleeve 30. The sleeve 30 originates at the shoulder 105 and extends downward, inferiorly along the arm away from the shoulder. The base 20 is joined with the sleeve 30 to cover the arm of the wearer. This can provide relatively constant compression over shoulder and torso of wearer to improve circulation and to enhance heat retention.

The sleeve 30 can be in the form of a tube, which can circumferentiate the upper arm of the wearer. The sleeve 30 can further extend over the biceps and triceps of the wearer, on the respective anterior and posterior sides of the upper arm. In some cases, the sleeve 30 can also extend superior to the upper arm, over a portion of the shoulder 105 of the wearer 100.

The orthosis 10 can include sleeve posterior/anterior strap anchors 28A and 28P. In the current embodiment, the ends of the posterior/anterior straps are permanently stitched to the sleeve anchor points 28A, 28P. In an alternative embodiment, the sleeve anchors 28A, 28P can be hook or loop surfaces that cooperate with hook or loop surfaces of the straps to secure the lateral ends 42, 52 of the anterior stability strap 40 and posterior stability strap to the sleeve 30. In yet other alternative embodiments, the sleeve anchors 28A, 28P can be adjustable D-type loops, buckles, or the like that secure respective portions of the strap ends 42, 52 instead of hook or loop surfaces.

The orthosis can also include a bicep anchor 250 fixedly and immovably joined with the sleeve 20, generally disposed at the center of the sleeve along its vertical symmetry line. As shown in FIG. 4, the bicep anchor 250 can define a channel through which the bicep strap can be routed. The channel can be formed in a similar fashion as the channel 60C in the symmetrical anchor 60. Like the symmetrical anchor channel, the bicep channel optionally can be in the form of a sheath simply stitched to the underlying panel. The bicep strap 70 can be slidably disposed within the bicep channel so it can freely move therein. Due to the shape of the channel, the anchor redirects the strap 70 through it about the sleeve in a curved manner, wrapping the bicep strap 70 around the circumference of the sleeve 30.

As depicted in FIG. 4, the bicep strap 70 can be routed through the sleeve anchor 250 and wrapped around the edge of the sleeve 30, and both ends can be secured to the sleeve or the back of the anterior/posterior straps. As depicted in FIG. 4, one end 71 of the bicep strap with a hook portion 75 is selectively secured to the loop surface disposed on the back of the anterior stability strap 40. Further, the other end 72 of the bicep strap can be selectively secured to the loop surface disposed on the back of the posterior stability strap 50. The bicep strap 70 can aid in ensuring the lateral ends 42, 52 of the posterior and anterior straps stay fixed in place while the other ends 41, 42 are being adjusted.

As mentioned above, the orthosis 10 can include anterior stability strap 40 and a posterior stability strap 50. Each of these straps can optionally be elastic and configured to store respective tension forces TF1 and TF2. The anterior stability strap 40 includes a first end 41 and a second end 42. In the current embodiment, the primary end 41 is removably or selectively anchored to the base 20, generally on the torso strap 31. The anterior stability strap 40 also includes an intermediate part 43 that extends between the first end 41 and the second end 42.

As mentioned above, the anterior stability strap includes the primary intermediate part 43. This part 43 extends upwardly from the primary anterior end 41, over an anterior portion of the base and across the shoulder 105 of the wearer. It further transitions rearward to a posterior portion 30P of the base/sleeve. The intermediate part 43 also extends over this posterior portion 30P and underneath the wearer's arm. The intermediate part 43 wraps around the anterior portion 30A of the sleeve to the second end 42 of the strap 40. This second end 42 can be disposed adjacent the anterior portion 30A of the sleeve or base, depending on the desired tensioning of the anterior strap 40.

As shown in FIG. 3, the first and second ends 41, 42 can be in a fixed position relative to the base, sleeve, and wearer in general. These components can be constructed so that they do not move relative to those elements. The intermediate part 43 between these ends however can be configured to stretch and to store a tension force TF1 generally within the anterior stability strap, between the respective first and second ends 41, 42 or more generally between where the strap ends 41, 42 are anchored respectively on the sleeve and torso strap.

With the configuration of the anterior stability strap, its ends and intermediate part, that component can be adjusted to establish a predetermined tension force TF1 within the intermediate part and the strap. Due to the routing of the anterior stability strap 40, the strap can be used to provide inferior and posterior support to the glenohumeral joint of the wearer. To provide adjustment, the selectively attachable end 41 can be removed from its hook-and-loop fastener to move that end relative to the opposite, fixed, end. A wearer or a healthcare provider can pull, or otherwise extend the selectively fixable end 41 to increase a tension force TF1 stored in the anterior stability strap. The precise preselected tension force TF1 can be selected to address the degree of instability or joint laxity in the glenohumeral joint. After the end 41 is adjusted, and the predetermined tension force TF1 achieves a desired level, for example, by changing the tension force TF1 from a first force to a second greater force, the end 41 can be engaged to fix the strap end at a fixed location and orientation—for example by refastening the end 41 to the hook-and-loop surface. The posterior stability strap 50 can be adjusted in a similar manner.

Optionally, during the adjustment of the tension force TF1 in the anterior stability strap 40, as well as any other straps mentioned herein, such as the posterior stability strap, or the sleeve strap or hammoock strap, the general pathing of the strap remains substantially static, that is, the same, even when the tension force of the respective straps are changed. While the precise position and orientation of the anterior strap may be changed via this adjustment, the intermediate part 43 of the strap follows the same general path across the orthosis.

Figure 1C:
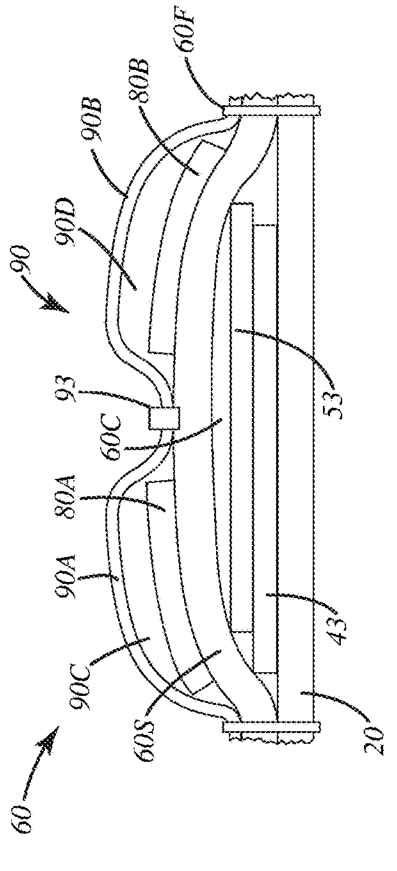
FIG. 1C is a section view taken along lines 1C-1C of FIG. 3.

The orthosis 10 also can include a symmetrical anchor 60 fixedly and immovably joined with the base 20, generally adjacent the shoulder 105. As shown in FIGS. 1A-C, the symmetrical anchor 60 can define a channel 60C. This channel can be defined between an overlapping panel 60S that is joined to the underlying base 20 via a fastening element 60F. As shown, the fastening element 60F can be in the form of stitching, but of course can be other fastening devices, such as glue, cement, a hot weld, fasteners or the like. Further the channel optionally can be in the form of a sheath simply stitched to the underlying panel. The anterior stability strap 40 can be slidably disposed within the channel 60C so it can freely move therein. Due to the curvature of the symmetrical anchor, perhaps as best shown in FIGS. 3-4, that anchor redirects the strap 40 through it inferiorly and in a curved manner, wrapping the anterior stability strap 40 downward and behind to the posterior 30P of the sleeve or base.

Optionally, due to the slidable relationship between the anchor 60 and the anterior stability strap, the anterior stability strap can be constrained to extend and move substantially only along a permanent first fixed route so that the anterior stability strap cannot be rerouted along a different route over the shoulder. For example, as shown in FIG. 3, the anterior stability strap 40 can extend along fixed route or pathway FR1. Generally, due to the constraints of the intermediate part 43 by the anchor 60 and the ends being fastened with hook and loop fasteners, this strap cannot move or slide across the sleeve and/or base or generally across the shoulder of a wearer to deviate from this fixed route FR1. With this type of fixed routing, the anterior stability strap can be fixed at a desired route by the manufacturer of the orthosis. Optionally, that route is configured so that it cannot be changed by a later user or a wearer of the orthosis. In turn, this can reduce the complexity of the orthosis and its operation for users and wearers. Further optionally, the user can make an adjustment of the tension forces in the anterior stability strap or other straps as described further below. The user in this case need not be concerned with the particular routing of the stability straps over the shoulder, relative to the glenohumeral joint.

As mentioned above, the orthosis 10 also can include a posterior stability strap 50. This posterior stability strap 50 can include a first end 51 and a second end 52, perhaps best shown in FIG. 3. Between these ends an intermediate part 53 is disposed. The first end 51 can be fastened to the base with hook and loop fasteners, similar to the hook and loop fasteners described in conjunction with the anterior stability strap 40. The second end 52 can be joined with the sleeve with hook and loop fasteners similar to the end 42 of the anterior stability strap 40. In addition, the posterior strap can be guided by the symmetrical anchor 60 described above. As discussed above, the symmetrical anchor can define a channel 60C as shown in FIG. 1C for the anterior stability strap 40. The channel 60C can be sized and shaped to accommodate both intermediate parts 43, 53 of the anterior stability strap 40 and the posterior stability strap 53 simultaneously.

As shown in FIG. 1C and FIG. 3, the intermediate part 53 of the posterior stability strap 50 can be slidably disposed in the symmetrical anchor channel 60C. The posterior stability strap 50 can be joined and fixedly anchored to the base posterior surface 24 or torso strap surface 33, with hook and loop fasteners. The posterior stability strap 50 also can include as mentioned above the intermediate part 53 that extends upwardly from the posterior end 51, over a posterior portion of the base and across the shoulder 105 of the wearer. It further transitions forward to an anterior portion 30A of the base/sleeve. The intermediate part 53 also extends over this anterior portion 30A and underneath the wearer's arm. The intermediate part 53 wraps around the posterior portion 30A of the sleeve to the second end 52 of the strap 50. This second end 52 can be disposed adjacent the posterior portion 30P of the sleeve or base, depending on the desired tensioning of the posterior strap 50. This can provide the preselected tension force TF2. With this selective adjustment of the tension force TF2, a user can provide anterior and/or inferior support to the glenohumeral joint of the wearer 100. In addition, the posterior strap can provide proprioceptive feedback to the wearer so that the wearer can feel when the arm is rotated externally to a position that could compromise the glenohumeral joint and previous surgical repairs relative thereto.

As can be appreciated from FIGS. 1A-C and 3-4, the intermediate parts 53 and 43 of the respective posterior stability strap and anterior stability strap can crisscross or otherwise traverse one another on the shoulder 105, and in particular within the channel of the symmetrical anchor 60.

Figure 8B:
FIGS. 8A-8D illustrates a donning and tensioning procedure for the shoulder brace of FIGS. 1A-C.
Figure 8A:
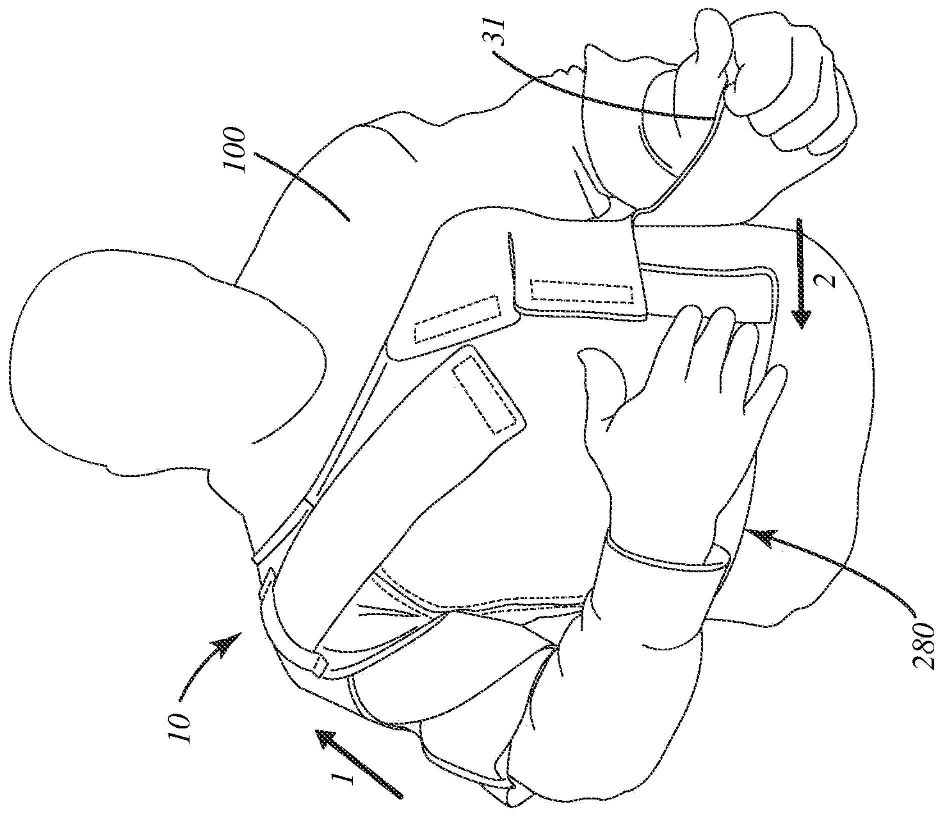

Donning the orthosis 10 along with operation of the anterior stability strap 40 can be understood with reference to FIGS. 8A-D. As shown in FIG. 8A, to begin donning the orthosis, the wearer 100 places their arm in the sleeve 30 of the compression mitt 280 and pulls it toward their neck to ensure proper location of the straps relative to the wearer's shoulder. The brace 10 is closed by wrapping the torso strap 31 around the chest/torso and securing the hook and loop panels to the hook and loop surfaces of the compression mitt 280. As shown in FIG. 8B, the hook and loop bicep closure can be wrapped and secured around the bicep at the desired tension.

Figure 8D:
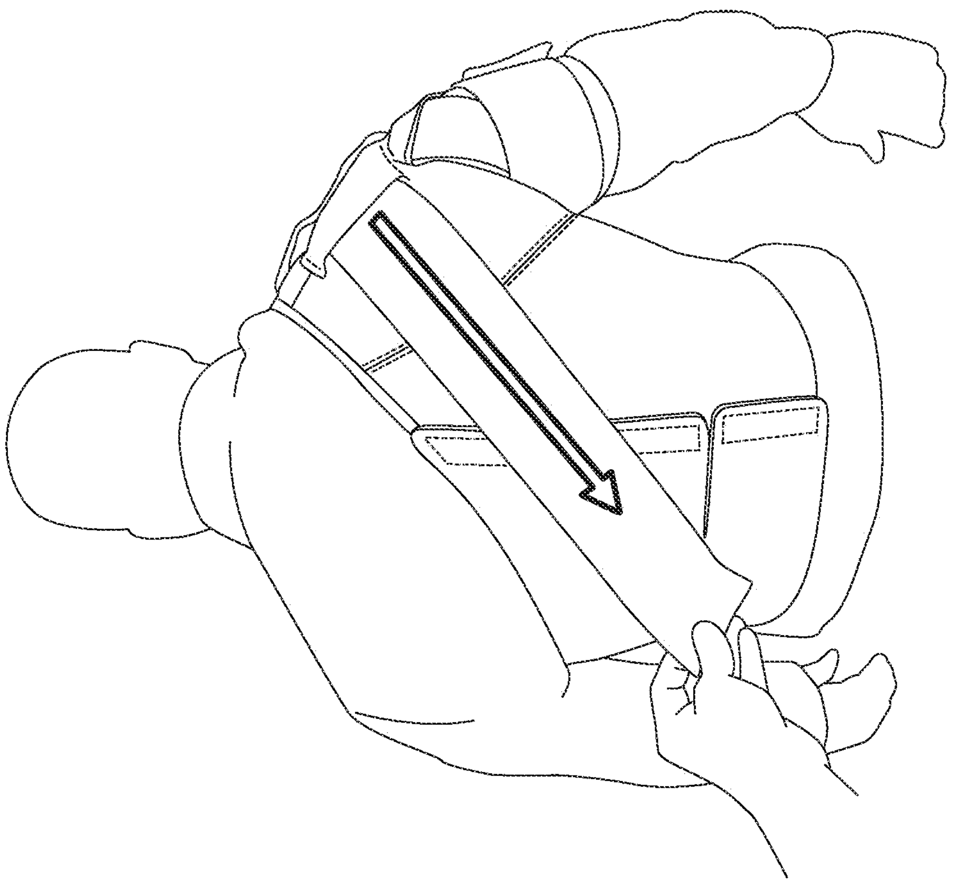
Figure 8C:
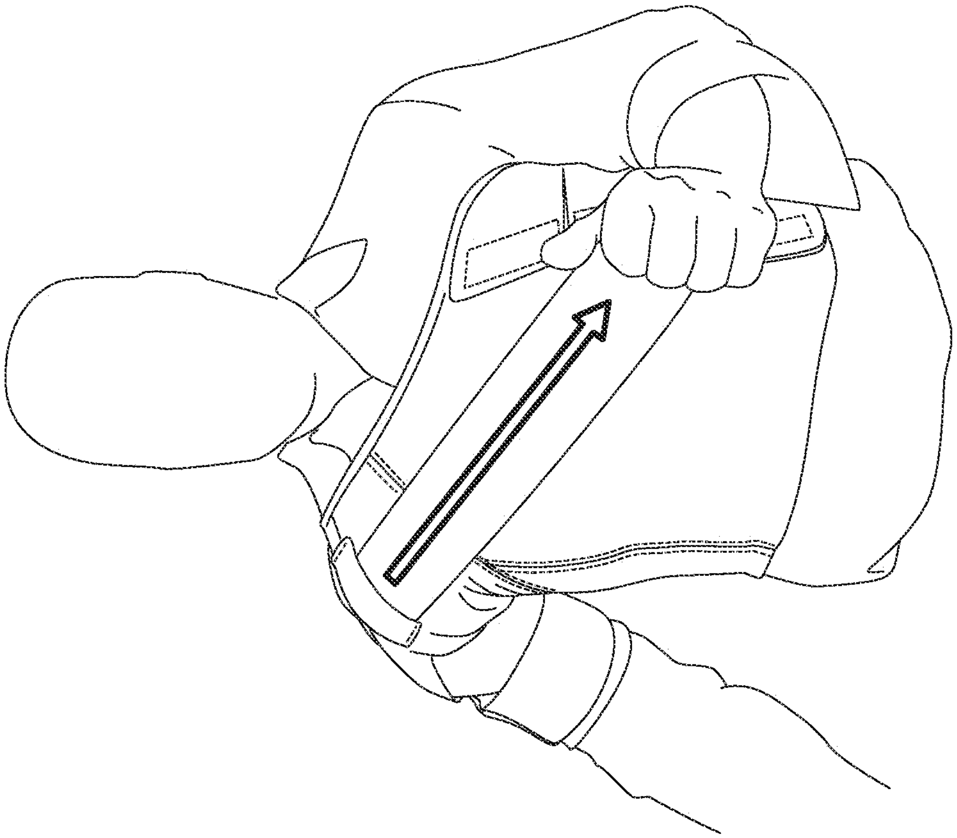

As shown in FIG. 8C, the anterior wind-up strap can be tensioned. The anterior stability strap 40 is placed in an adjustment mode. A user grasps the end 41 of the strap (releasing it from the hook and loop fastener on the compression mitt if necessary). The user can exert a force P1 to pull the end 42 under force. Because the strap, in particular the intermediate part 43, is constrained by the symmetrical anchor 60 with its channel 60C, the stability strap 40 does not move relative to the shoulder, the sleeve, and the like during the pulling. The opposite end 42 also remains static due it being fastened at the sleeve. After the user determines that the first tension force TF1 in the stability strap is appropriate to address the instability in the wearer's shoulder or glenohumeral joint, the user can fix the end 41 by securing it to the hook and loop fastener surface of the torso strap near the axilla of the unbraced arm. When this occurs, the strap exerts the stored tension force TF1. As a result, the tension force TF1 in the strap operates to provide inferior and posterior support to the glenohumeral joint of the wearer. As shown in FIG. 8D, the posterior wind-up strap can be tensioned in a similar fashion. The user grasps and releases the hook and loop fastened end, pulls the strap to create the desired tension and secures the hook and loop fastener on the back of the torso strap near the axilla of the unbraced arm.

Figures 7A, 7B:
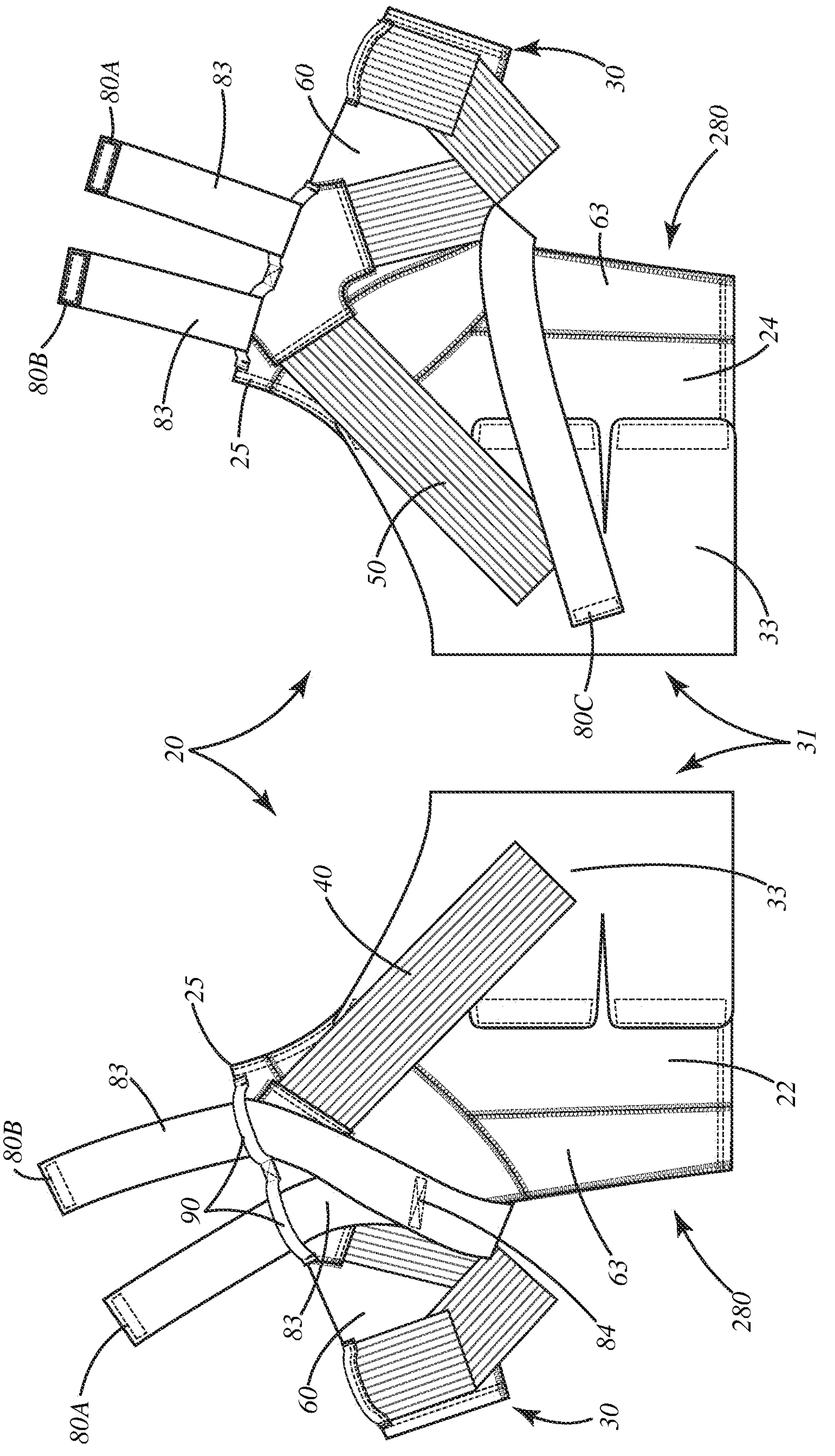
FIG. 7A is a front view of the shoulder brace with wind-up straps and a hammock strap partially equipped.
FIG. 7B is a rear view of the shoulder brace with wind-up straps and a hammock strap partially equipped.

Optionally, the orthosis 10, as shown in FIGS. 1A-C and 7A-B, and 9A-C can include a hammock stability strap 80. The hammock stability strap can include a tensioning end 80C, an opposite end (in this embodiment two bifurcated ends 80A, 80B), and an intermediate portion 83 extending between the tensioning end and the opposite or two bifurcated ends, in embodiments with bifurcated ends, the intermediate portion 83 can include a bifurcation crease 84. The opposite end (e.g., two bifurcated ends 80A, 80B) can fixedly and removably or selectively connect near the center of the wearer's back on the posterior of the base 20. As shown in FIGS. 7A-B the intermediate portion 83 can extend over the shoulder of the wearer, transitioning under the axilla of the wearer's arm with the bifurcation crease 84 of the intermediate portion being disposed near the axilla and lateral border of the pectoralis and further transitioning around the torso of the wearer. The tensioning end 80C can wrap under the axilla of the braced arm and can be secured on the posterior of the base 20 so that a preselected tension in the hammock stability strap 80 can be established by the wearer or a healthcare provider, thereby providing anterior, inferior and multi-directional support to a glenohumeral joint of the wearer. Each of the ends 80A, 80B, 80C includes a respective hook or loop surface 85A, 85B, 85C for selective connection to a counterpart hook or loop surface of the base 20 or the anterior/posterior straps 40, 50 (e.g., surface 33). While installed, the hammock strap can be under tension forces TF3A, TF3B, TF3C (see FIG. 9A-C) to effectively bolster anterior/inferior support for the glenohumeral joint 105G of the wearer.

Optionally, the tension force in this hammock strap can increase during external rotation and abduction to provide a "wind-up" effect, similar to that described above in connection with the anterior strap. This can increase proprioception, during external rotation and abduction, typically a vulnerable position for a wearer with anterior/inferior instability. In turn, the wearer can better perceive the vulnerability in that position due to the tension in the strap. The hammock strap essentially acts similarly to the Inferior Glenohumeral Ligament (IGHL) to prevent anterior dislocation while in external rotation and abduction.

Perhaps as best shown in FIGS. 1C and 7A-B, the orthosis 10 can include a hammock strap shoulder anchor 90 joined to the base 20 and/or symmetrical anchor 60. The hammock strap anchor 90 can be fixedly and immovably and/or permanently joined with the base and/or anchor 60 and can define channels similar to those described above in connection with the other stability straps. The hammock anchor 90 can include a stitch 93 toward the center of the anchor 60S. In particular, the stitch 93 can separate the hammock strap anchor 90 into two separate hammock strap loops or anchors 90A, 90B, each defining a separate channel 90C, 90D that each can accommodate one of the bifurcated ends 80A, 80B of the hammock strap. The two hammock strap loops 90A, 90B assist in routing and positioning the hammock stability strap 80 relative to the base. In alternative embodiments, for example those without bifurcated ends, the hammock anchor 90 may include a single channel for routing and anchoring the hammock strap. In some embodiments, the hammock strap shoulder anchor 90 is joined entirely to the shoulder anchor 60 that is fixedly and immovably joined with the shoulder portion of the compression mitt. In other embodiments, the hammock strap shoulder anchor 90 is joined partially to the anchor 60 and partially to the compression mitt 280 or base 20. Specifically, the hammock strap anchor 90 is at least one of stitched, welded and adhered permanently to form the pair of hammock strap channels 90C, 90D, wherein the pair of hammock strap channels assist in routing and positioning the bifurcated ends of the hammock stability strap relative to the base.

The intermediate part 83 of the hammock strap can be slidably disposed in hammock strap channels 90C, 90D. This can ensure that the strap is guided over the shoulder in a consistent and precise manner. The bifurcated ends 80A, 80B and the tensioning end 80C can each be fixed using anchors surfaces similar to the anchors 28A and 28P described above for adjustment of the anterior and posterior strap ends. For example, each end of the hammock strap can include a hook or loop surface 85A, 85B, 85C for selective connection to a counterpart hook or loop surface of the base 20 or the back of the anterior/posterior straps 40, 50.

Figure 9C:
FIGS. 9A-9C illustrates an installation and tensioning procedure for the hammock strap of 6A-B onto the shoulder brace of FIGS. 1A-C.
Figure 9B:
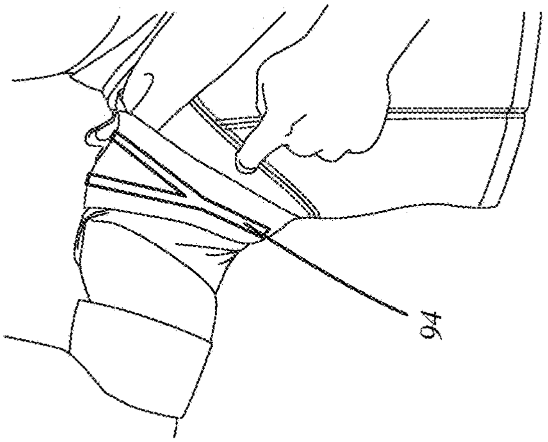
Figure 9A:
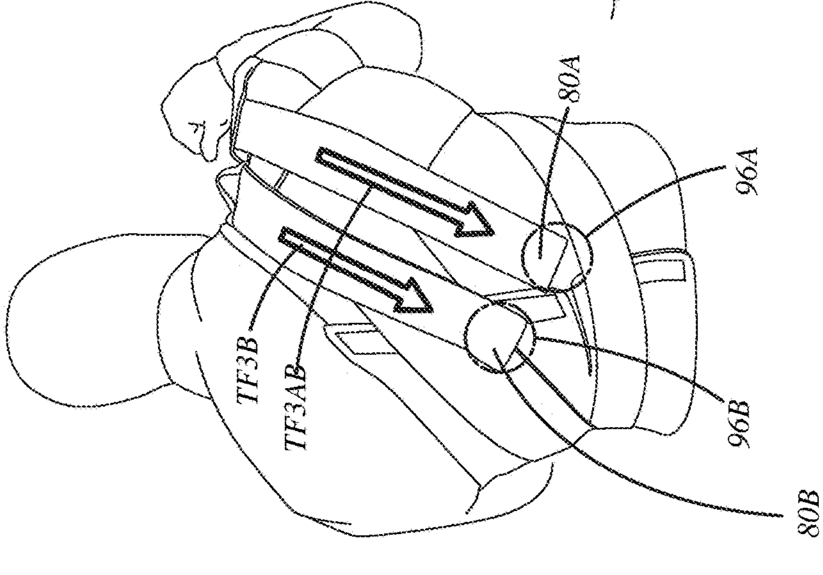

Installation and operation of the hammock strap is described in connection with FIGS. 7A-B and 9A-C. To install the hammock strap, the bifurcated ends of the hammock strap 80A, 80B are routed through the channels 90C, 90D of the hammock strap loops 90A, 90B of the hammock strap anchor 90, perhaps as best illustrated in FIGS. 7A-B. Using hook and loop fasteners, the bifurcated ends 90A, 90B of the hammock strap 80 can be secured near the center of the wearer's back, as illustrated in FIG. 9A. The anchor points 96A, 96B of the ends 80A, 80B can be selected as the user sees fit. As depicted, the hook and loop fastener connection can be made essentially anywhere on the base because the various surfaces (e.g., on the compression mitt and back of the posterior strap 50) include a loop surface or zone to facilitate a wide area of connection points. As shown in FIG. 9B, to provide suitable support, the bifurcation crease 94 can be positioned near the front of the axilla and lateral border of the pectoralis. Referring to 9C, the tensioning end 90C of the hammock strap can be pulled under the axilla of the braced arm and secured with hook and loop fasteners on the posterior side of the base (e.g., to the base itself or the back of the posterior strap). If desired, the tensioning strap can be pulled around to the anterior side of the torso, under the unbraced arm to provide a desired level of support. While installed and tensioned, the hammock strap can be under tension forces TF3A, TF3B, TF3C (see FIGS. 9A-C) to effectively bolster anterior/inferior support for the glenohumeral joint 105G of the wearer. That is, the hammock strap tension can be adjusted until forces TF3A, TF3B and TF3C achieve a desired level to address anterior, inferior, and multidirectional instability and provide corresponding support to the glenohumeral joint of the wearer. During the adjustment, the hammock strap maintains its pathing along its fixed route, constrained by the hammock anchor 90 and its respective bifurcated channels 90C, 90D. Thus, upon the pulling on the tensioning end 80C, primarily only the tension is adjusted in the respective bifurcated straps 80A, 80B rather than position or orientation of those straps. After the adjustment is complete, the tensioning end 80C is secured using fastener 85C and the tension forces are stored to provide the desired support.

In some alternative embodiments, the hammock strap can be reversed to provide posterior/inferior support. That is, the opposite or bifurcated end can be routed through the shoulder anchor in the opposite direction such that it joins to the anterior surface of the base instead of the posterior surface. The opposite end (e.g., two bifurcated ends 80A, 80B) can fixedly and removably or selectively connect near the center of the anterior of the base 20. The intermediate portion 83 can extend over the shoulder of the wearer, transitioning under the axilla of the wearer's arm with the bifurcation crease 84 (if included) of the intermediate portion being disposed near the axilla and lateral border of the pectoralis and further transitioning around the torso of the wearer. The tensioning end 80C can wrap under the axilla of the braced arm and can be secured on the anterior of the base 20 so that a preselected tension in the hammock stability strap 80 can be established by the wearer or a healthcare provider, thereby providing anterior, inferior, and multi-directional support to a glenohumeral joint of the wearer.

Figure 6B:
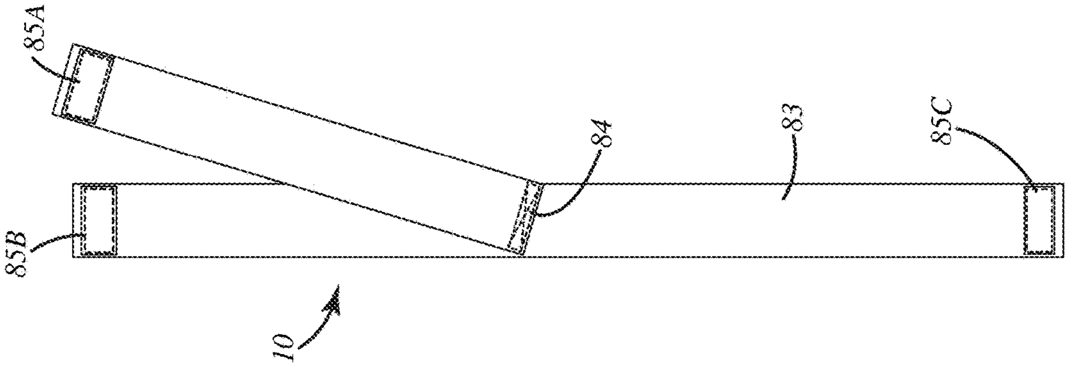
FIG. 6B is a back view of a removable hammock strap.
Figure 6A:
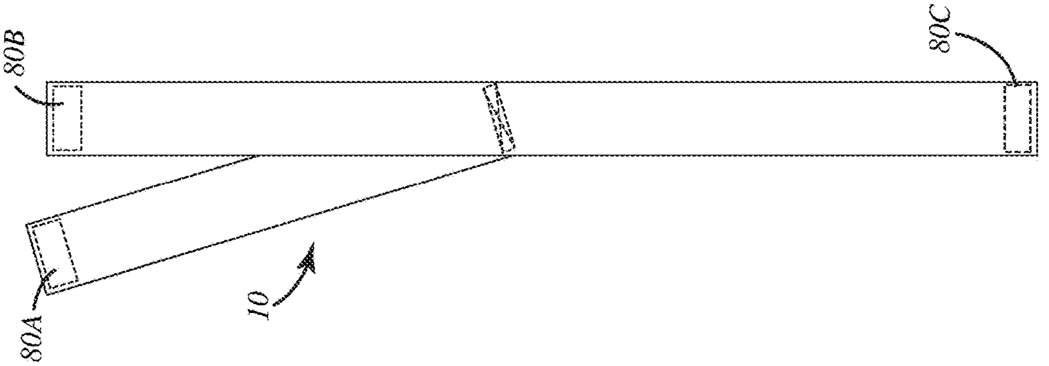
FIG. 6A is a front view of a removable hammock strap.

Further, in some embodiments, the hammock strap is universal in that it can be utilized regardless of the shoulder the brace is being installed on. That is, the hammock strap can be utilized to provide support to the left or right shoulder. In other embodiments, a left shoulder hammock strap and right shoulder hammock strap can be provided that are specifically designed for supporting the left and right shoulders specifically. For example, the bifurcation crease 84 can be stitched an angle (e.g., as shown in FIG. 6A, one bifurcated end 80A is offset about 30 degrees from the centerline of the hammock strap and other bifurcated end 80B) such that one of the bifurcated ends is aligned with the tensioning end while the other is offset at an angle.

In the orthosis of the current embodiments, the stability straps optionally are automatically aligned with designated, fixed tension force pathways upon donning the brace to address respective anterior, posterior, multidirectional instabilities. With this embodiment, one might only tighten the straps to apply the desired tension therein, rather than reorient the straps relative to the sleeve and/or the base or the anatomy of the wearer.

Optionally, the respective channels can be outfitted with a covering, stiffening agent or low friction materials to enhance sliding and/or movement of the respective straps within. Further optionally, while a strap is configured to slide within the channel, that strap need not necessarily slide throughout the entire channel. For example, certain portions of the strap can be stitched or secured to the primary or secondary layers so that they are generally immovable, while other portions are not stitched or secured, and generally are able to move via a sliding action.

Other alternative embodiments of the orthosis are contemplated. In one embodiment, any of the posterior, anterior and/or hammock stability straps can be constructed from an inelastic material, rather than an elastic material. In this case, any one of the straps can be designated as an immobilizing strap to control and limit the range of motion of the joint, for example the glenohumeral joint. The current embodiments above can be outfitted so that the elastic straps are substituted with one or more inelastic straps, adjustable or not, to provide such immobilization.

In yet another embodiment, any one of the anterior, posterior and/or hammock straps can include indicia along the length. This indicia can be in the form of alphanumeric elements and/or in the form of color coding on the straps. This can provide feedback to the user and/or wear as to the degree of adjustment of the straps during such adjustment. Optionally, the orthosis can include a spring-loaded dial in line with the straps and integrated into the anchors to provide precise registration of the tension force stored in the respective straps.

It still another embodiment, the orthosis can include a removable pad that is disposed on the shoulder region of the base for players with instability, to disperse impact forces. The pad can be fastened to the base and/or the bolster element using a variety of fasteners such as those described herein. In still another embodiment the base and sleeve can be perforated or otherwise include venting throughout the chest and back to increase breathability. Alternative breathable materials and/or open mesh materials can be used to construct the base and/or sleeve.

In still a further alternative embodiment, the orthosis can be in the form of a shirt. The shirt can be constructed from an engineered mesh material to control tension forces along lines discussed herein. In this construction, for example the textile over the shoulder and arm can mimic the support provided by the glenohumeral ligaments to provide desired support and to address instability and/or joint laxity.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The invention claimed is:

1. A reversible shoulder orthosis comprising:

a reversible base that includes a vertically symmetrical torso portion configured to extend around a torso of a wearer and a vertically symmetrical compression mitt including a shoulder portion for extending generally across a glenohumeral joint of the wearer from a base anterior to a base posterior and a sleeve portion configured to extend over an upper arm of the wearer, the reversible base configured to secure the reversible shoulder orthosis to the wearer;

an anterior stability strap having a proximal anterior end, intermediate portion, and a distal sleeve end, the proximal anterior end being removably or selectively joined to the reversible base on an anterior of the base, the anterior stability strap including an intermediate part that extends from the proximal anterior end, over an anterior portion of the shoulder portion of the reversible base, and transitions rearward to a posterior portion of the shoulder portion of the reversible base, extending over the posterior portion to the distal sleeve end of the anterior stability strap, which is disposed on the sleeve portion of the reversible base, the proximal anterior end being adjustably joined with the reversible base so that a preselected tension in the anterior stability strap can be adjusted, thereby providing inferior and posterior support to a glenohumeral joint of the wearer;

a posterior stability strap having a proximal posterior end, intermediate portion, and a distal sleeve end, the proximal posterior end being selectively joined to the reversible base on a posterior of the base, the posterior stability strap including an intermediate part that extends from the proximal posterior end, over a posterior portion of the shoulder portion of the reversible base, and transitions forward to an anterior portion of the shoulder portion of the reversible base, extending over the anterior portion to the distal sleeve end of the posterior stability strap, which is disposed on the sleeve portion of the reversible base, the proximal posterior end being adjustably joined with the reversible base so that a preselected tension in the posterior stability strap can be adjusted, thereby providing anterior and inferior support to the glenohumeral joint of the wearer.

2. The orthosis of claim 1 comprising:

a symmetrical shoulder anchor fixedly and immovably joined with the shoulder portion of the vertically symmetrical compression mitt, the symmetrical shoulder anchor defining an anchor channel, wherein the anterior stability strap intermediate part and the posterior stability strap intermediate part are both slidably disposed in the anchor channel.

3. The orthosis of claim 2, wherein the symmetrical shoulder anchor is at least one of stitched, welded and adhered permanently to the shoulder portion of the vertically symmetrical compression mitt so that the symmetrical shoulder anchor cannot be removed from the compression mitt without destroying at least one of the symmetrical compression mitt and the symmetrical shoulder anchor.

4. The orthosis of claim 1 comprising:

a hammock stability strap having a tensioning end, an opposite end, and an intermediate portion extending between the tensioning end and the opposite end;

the opposite end selectively joined to the posterior of the reversible base, the intermediate portion extending over the shoulder of the wearer, transitioning under the axilla of the wearer's arm with the intermediate portion being at least partially disposed near the axilla and lateral border of the pectoralis, and further transitioning around the torso of the wearer, the tensioning end being selectively joined with the reversible base so that a preselected tension in the hammock stability strap can be established by the wearer or a healthcare provider, thereby providing inferior and multi-directional support to a glenohumeral joint of the wearer.

5. The orthosis of claim 4 including a hammock strap shoulder loop joined to the base, wherein the hammock strap shoulder loop assists in routing and positioning the hammock stability strap relative to the base.

6. The orthosis of claim 4 wherein, the opposite end includes two bifurcated ends, and the intermediate portion extends between the tensioning end and the two bifurcated ends, the intermediate portion including a bifurcation crease;

the two bifurcated ends of the opposite end selectively joined to the posterior of the reversible base, the intermediate portion extending over the shoulder of the wearer, transitioning under the axilla of the wearer's arm with the bifurcation crease of the intermediate portion being disposed near the axilla and lateral border of the pectoralis, and further transitioning around the torso of the wearer, the tensioning end being selectively joined with the reversible base.

7. The orthosis of claim 6 including a pair of hammock strap shoulder loops joined to the base, wherein the pair of hammock strap shoulder loops assist in routing and positioning the hammock stability strap relative to the base.

8. The orthosis of claim 1 wherein the shoulder compression mitt, the anterior stability strap and the posterior stability strap are all fixed in a respective permanent orientation relative to the sleeve and relative to one another, but wherein the anterior stability strap and the posterior stability strap are free to slide along a respective first fixed route and a second fixed route.

9. The orthosis of claim 1 including a bicep loop and a bicep strap routed through the bicep loop around the bicep of the wearer.

10. The orthosis of claim 1 wherein the vertically symmetrical torso portion of the base includes a plurality of panels, each having a hook or loop surface disposed on the interior surface of the plurality of panels for securing the torso portion to the compression mitt portion.

11. The orthosis of claim 1 wherein the vertically symmetrical torso portion of the base includes an exterior hook or loop surface for selectively joining the anterior stability strap and the posterior stability strap.

12. A shoulder orthosis comprising:

a base that includes a torso portion configured to extend around a torso of a wearer and a compression mitt including a shoulder portion for extending generally across a glenohumeral joint of the wearer from a base anterior to a base posterior and a sleeve portion configured to extend over an upper arm of the wearer, the base configured to secure the shoulder orthosis to the wearer;

an anterior stability strap having a proximal anterior end, intermediate portion, and a distal sleeve end, the proximal anterior end being selectively joined to the base on an anterior of the base, the anterior stability strap including an intermediate part that extends from the proximal anterior end, over an anterior portion of the shoulder portion of the base, and transitions rearward to a posterior portion of the shoulder portion of the base, extending over the posterior portion to the distal sleeve end of the anterior stability strap, which is disposed on the sleeve portion of the base, the proximal anterior end being adjustably joined with the base so that a preselected tension in the anterior stability strap can be adjusted, thereby providing inferior and posterior support to a glenohumeral joint of the wearer;

a posterior stability strap having a proximal posterior end, intermediate portion, and a distal sleeve end, the proximal posterior end being selectively joined to the base on a posterior of the base, the posterior stability strap including an intermediate part that extends from the proximal posterior end, over a posterior portion of the shoulder portion of the base, and transitions forward to an anterior portion of the shoulder portion of the base, extending over the anterior portion to the distal sleeve end of the posterior stability strap, which is disposed on the sleeve portion of the base, the proximal posterior end being adjustably joined with the base so that a preselected tension in the posterior stability strap can be adjusted, thereby providing anterior and inferior support to the glenohumeral joint of the wearer;

a hammock stability strap having a tensioning end, an opposite end, and an intermediate portion extending between the tensioning end and the opposite end;

the opposite end selectively joined to the posterior of the base, the intermediate portion extending over the shoulder of the wearer, transitioning under the axilla of the wearer's arm with the intermediate portion being at least partially disposed near the axilla and lateral border of the pectoralis, and further transitioning around the torso of the wearer, the tensioning end being selectively joined with the base so that a preselected tension in the hammock stability strap can be established by the wearer or a healthcare provider, thereby providing inferior and multi-directional support to a glenohumeral joint of the wearer.

13. The orthosis of claim 12 including a hammock strap shoulder loop joined to the base, wherein the hammock strap shoulder loop assists in routing and positioning the hammock stability strap relative to the base.

14. The orthosis of claim 12 wherein, the opposite end includes two bifurcated ends, and the intermediate portion extends between the tensioning end and the two bifurcated ends, the intermediate portion including a bifurcation crease;

the two bifurcated ends of the opposite end selectively joined to the posterior of the base, the intermediate portion extending over the shoulder of the wearer, transitioning under the axilla of the wearer's arm with the bifurcation crease of the intermediate portion being disposed near the axilla and lateral border of the pectoralis, and further transitioning around the torso of the wearer, the tensioning end being selectively joined with the base.

15. The orthosis of claim 14 including a pair of hammock strap shoulder loops joined to the base, wherein the pair of hammock strap shoulder loops assist in routing and positioning the hammock stability strap relative to the base.

16. The orthosis of claim 12 including a shoulder anchor fixedly and immovably joined with the shoulder portion of the compression mitt, the shoulder anchor defining an anchor channel, wherein the anterior stability strap intermediate part and the posterior stability strap intermediate part are both slidably disposed in the anchor channel and the anterior stability strap and the posterior stability strap are configured to traverse over one another.

17. The orthosis of claim 16, wherein the shoulder anchor is at least one of stitched, welded and adhered permanently to the shoulder portion of the compression mitt so that the shoulder anchor cannot be removed from the compression mitt without destroying at least one of the compression mitt and the shoulder anchor.

18. The orthosis of claim 17 including hammock strap shoulder loop wherein the hammock strap shoulder loop is at least one of stitched, welded and adhered permanently to the shoulder anchor to separating the hammock strap shoulder loop into a pair of hammock strap channels, wherein the pair of hammock strap channels assist in routing and positioning the bifurcated ends of the hammock stability strap relative to the base.

19. The orthosis of claim 12 wherein the torso portion is vertically symmetrical and the compression mitt is vertically symmetrical such that the base is reversible and wearable on either a left or right arm of the wearer.

20. The orthosis of claim 12 wherein the shoulder compression mitt, the anterior stability strap, the posterior stability strap, and the hammock stability strap are all fixed in a respective permanent orientation relative to one another, but wherein the anterior stability strap and the posterior stability strap are free to slide along a respective first fixed route and a second fixed route.

21. The orthosis of claim 12 including a bicep loop and a bicep strap routed through the bicep loop around the bicep of the wearer.

22. The orthosis of claim 12 wherein the torso portion of the base includes a plurality of panels, each having a hook or loop surface disposed on the interior surface of the plurality of panels for securing the torso portion to the compression mitt portion.

23. The orthosis of claim 12 wherein the torso portion of the base includes an exterior hook or loop surface for selectively joining the anterior stability strap and the posterior stability strap.

* * * * *